US012565478B1

(12) United States Patent
Tabuteau

(10) Patent No.: US 12,565,478 B1
(45) Date of Patent: Mar. 3, 2026

(54) (S)-2-((S)-(2-ETHOXYPHENOXY)(PHENYL) METHYL)-4-NITROSOMORPHOLINE

(71) Applicant: Axsome Therapeutics, Inc., New York, NY (US)

(72) Inventor: Herriot Tabuteau, New York, NY (US)

(73) Assignee: Axsome Therapeutics, Inc., New York, NY (US)

( * ) Notice: Subject to any disclaimer, the term of this patent is extended or adjusted under 35 U.S.C. 154(b) by 0 days.

(21) Appl. No.: 19/096,247

(22) Filed: Mar. 31, 2025

Related U.S. Application Data

(60) Provisional application No. 63/747,812, filed on Jan. 21, 2025.

(51) Int. Cl.
*C07D 265/30* (2006.01)
*A61K 9/20* (2006.01)
*A61K 31/5375* (2006.01)

(52) U.S. Cl.
CPC .......... *C07D 265/30* (2013.01); *A61K 9/2009* (2013.01); *A61K 9/2013* (2013.01); *A61K 9/2054* (2013.01); *A61K 9/2059* (2013.01); *A61K 31/5375* (2013.01)

(58) Field of Classification Search
CPC . A61K 31/5375; A61K 9/2054; A61K 9/2059
See application file for complete search history.

(56) References Cited

U.S. PATENT DOCUMENTS 4,415,547 A 11/1983 Yu et al.
5,358,970 A 10/1994 Ruff et al.
6,228,398 B1 5/2001 Devane et al.
6,395,788 B1 5/2002 Iglehart
6,441,038 B1 8/2002 Loder et al.
6,465,458 B1 10/2002 Wong et al.
6,485,746 B1 11/2002 Campbell et al.
6,610,690 B2 8/2003 Wong et al.
6,622,036 B1 9/2003 Suffin
6,632,451 B2 10/2003 Penhasi et al.
6,642,235 B2 11/2003 Wong et al.
6,703,389 B2 3/2004 Wong et al.
6,987,107 B2 1/2006 Wong et al.
7,241,762 B2 7/2007 Wong et al.
7,276,503 B2 10/2007 Wong et al.
7,317,011 B2 1/2008 Wong et al.
7,338,953 B2 3/2008 Wong et al.
7,723,334 B2 5/2010 Wong et al.
8,383,681 B2 2/2013 Roberts et al.
8,512,751 B2 8/2013 Rariy et al.
8,562,951 B2 10/2013 Suffin et al.
9,034,874 B2 5/2015 Wang et al.
9,211,293 B2 12/2015 Deaver et al.
9,216,182 B2 12/2015 Wang et al.
9,359,290 B2 6/2016 Khayrallah et al.
9,364,458 B2 6/2016 Huang et al.
9,624,192 B2 4/2017 Wang et al.
9,750,734 B2 9/2017 Mouthon et al.
9,763,884 B2 9/2017 Bloemers et al.
10,137,091 B2 11/2018 Mullen et al.
10,576,045 B2 3/2020 Nir
11,020,402 B2 6/2021 Tabuteau
11,135,226 B2 10/2021 Tabuteau
11,185,547 B2 11/2021 Tabuteau
11,351,175 B2 6/2022 Tabuteau
11,364,245 B2 6/2022 Tabuteau
11,883,408 B2 1/2024 Tabuteau
11,957,686 B2 4/2024 Tabuteau
12,115,165 B2 10/2024 Tabuteau
12,246,023 B2 3/2025 Tabuteau
2003/0040464 A1 2/2003 Wong et al.
2003/0133982 A1 7/2003 Heimlich
2004/0102440 A1 5/2004 Wong et al.
2005/0250803 A1 11/2005 Glue et al.
2006/0039890 A1 2/2006 Renshaw et al.
2008/0020039 A1 1/2008 Parikh et al.
2008/0103145 A1 5/2008 Wong et al.
2008/0261984 A1 10/2008 Hughes et al.
2009/0023705 A1 1/2009 Roberts et al.
2009/0143387 A1 6/2009 Amidon et al.
2009/0275562 A1 11/2009 Rao et al.
2009/0291953 A1 11/2009 Airoldi et al.
2010/0068389 A1 3/2010 Kalofonos et al.
(Continued)

FOREIGN PATENT DOCUMENTS

CL 200001765 7/2001
CL 200802868 1/2009
(Continued)

OTHER PUBLICATIONS

Zarmpi et al., "Biopharmaceutical aspects and implications of excipient variability in drug product performance" European Journal of Pharmaceutics and Biopharmaceutics 111 (2017) 1-15.
Arnold L. M., et al., "Safety and Efficacy of Esreboxetine in Patients With Fibromyalgia", Arthritis & Rheumatism, 2012, 64, 7, 2387-2397, DOI: 10.1002/art.34390 Abstract, Patients and Methods, Results, Discussion and p. 2388.
Rowe, "Handbook of Pharmaceutical Excipients", 5th edition 2006 (gmpua.com/RD/RD/HandbookPharmaceutical%20Excipients.pdf (pp. 132, 188, 346, 430, 731). (Year: 2006).
Lawson, "Emerging pharmacological strategies for the treatment of fibromyalgia" World J Pharmacology 2017; 6(1): 1-10.
(Continued)

*Primary Examiner* — Kevin E Weddington
(74) *Attorney, Agent, or Firm* — Procopio, Cory, Hargreaves & Savitch LLP

(57) ABSTRACT

(S)-2-((S)-(2-ethoxyphenoxy)(phenyl)methyl)-4-nitrosomorpholine is useful for analysis of a pharmaceutical composition. Also disclosed herein are methods of determining the quality of pharmaceutical compositions, and dosage forms comprising a reduced level of (S)-2-((S)-(2-ethoxyphenoxy)(phenyl)methyl)-4-nitrosomorpholine. Therapeutic uses of the pharmaceutical compositions and dosage forms are also described herein.

22 Claims, No Drawings

(56) References Cited

U.S. PATENT DOCUMENTS

| | | | |
|---|---|---|---|
| 2010/0104643 | A1 | 4/2010 | Wilding et al. |
| 2010/0160294 | A1 | 6/2010 | Rao et al. |
| 2011/0052648 | A1 | 3/2011 | Avramoff et al. |
| 2011/0245287 | A1 | 10/2011 | Holaday et al. |
| 2012/0035121 | A1 | 2/2012 | Rudnic et al. |
| 2013/0017262 | A1 | 1/2013 | Mullen et al. |
| 2014/0275244 | A1 | 9/2014 | Khayrallah et al. |
| 2016/0008352 | A1 | 1/2016 | Tabuteau |
| 2016/0128998 | A1 | 5/2016 | Tabuteau |
| 2016/0244426 | A1 | 8/2016 | Auberson et al. |
| 2019/0185438 | A1 | 6/2019 | Lederman et al. |
| 2019/0381056 | A1 | 12/2019 | Tabuteau |
| 2020/0147093 | A1 | 5/2020 | Tabuteau |
| 2020/0147094 | A1 | 5/2020 | Tabuteau |
| 2020/0147095 | A1 | 5/2020 | Tabuteau |
| 2020/0147096 | A1 | 5/2020 | Tabuteau |
| 2020/0197388 | A1 | 6/2020 | Bear et al. |
| 2021/0015823 | A1 | 1/2021 | Tabuteau |
| 2021/0100808 | A1 | 4/2021 | Tabuteau |
| 2021/0100809 | A1 | 4/2021 | Tabuteau |
| 2021/0169893 | A1 | 6/2021 | Tabuteau |
| 2021/0252007 | A1 | 8/2021 | Tabuteau |
| 2021/0369722 | A1 | 12/2021 | Tabuteau |
| 2022/0249501 | A1 | 8/2022 | Tabuteau |
| 2022/0280524 | A1 | 9/2022 | Tabuteau |
| 2022/0313699 | A1 | 10/2022 | Tabuteau |
| 2022/0362252 | A1 | 11/2022 | Tabuteau |
| 2024/0131031 | A1 | 4/2024 | Tabuteau |

FOREIGN PATENT DOCUMENTS

| | | | |
|---|---|---|---|
| CN | 102319226 | A | 1/2012 |
| EP | 1632235 | A2 | 3/2006 |
| EP | 1515959 | B1 | 8/2009 |
| EP | 1536791 | B1 | 1/2010 |
| EP | 2514417 | A2 | 10/2012 |
| EP | 3598975 | A1 | 1/2020 |
| GB | 2167407 | A | 5/1986 |
| WO | 9528148 | A1 | 10/1995 |
| WO | 0101973 | A2 | 1/2001 |
| WO | 0039072 | A1 | 7/2001 |
| WO | 0147503 | A1 | 7/2001 |
| WO | 2004010998 | A1 | 2/2004 |
| WO | 2006069030 | A1 | 6/2006 |
| WO | 2008137923 | A2 | 11/2008 |
| WO | 2009049215 | A1 | 4/2009 |
| WO | 2009062318 | A1 | 5/2009 |
| WO | 2010044016 | A1 | 4/2010 |
| WO | 2011107749 | A2 | 9/2011 |
| WO | 2011107750 | A2 | 9/2011 |
| WO | 2011107755 | A2 | 9/2011 |
| WO | 2018200775 | A1 | 11/2018 |
| WO | 2019245975 | A1 | 12/2019 |
| WO | 2020081461 | A1 | 4/2020 |
| WO | 0162236 | A1 | 8/2020 |
| WO | 2024263560 | A1 | 12/2024 |

OTHER PUBLICATIONS

Pfizer, "NCT00754221—Open Label Extension Study of [S,S]-Reboxetine in Patients With Fibromyalgia", clinicaltrials.gov, last update Dec. 17, 2019, retrieved Feb. 21, 2025 Title, Participation Criteria and Study Plan.

International Search Report and Written Opinion, PCT/US2025/021386, mailed Jun. 24, 2025.

Cioc, R.C., et al., "Formation of N-Nitrosamine Drug Substance Related Impurities in Medicines: A Regulatory Perspective on Risk Factors and Mitigation Strategies", Organic Process Research & Development, 2023.

Johnson, G., "Review of nitrosamine drug substance related impurities (NDSRI) in pharmaceutical drugs: Risk assessments, acceptable intakes and QSAR tools", Oct. 17, 2023.

U.S. Food and Drug Administration, "The Voice of the Patient", A series of reports from the FDA's Patient-Focused Drug Development Initiative, Narcolepsy, Jun. 2014, p. 25.

Pardi, et al., "Hydroxybutyrate/Sodium Oxybate, Neurobiology, and Impact on Sleep and Wakefulness", 2006, CNS Drugs 2006; 20(12): 993-1018.

Kallweit, et al., "Pharmacological management of narcololepsy with and without cataplexy", Expert Opinion on Pharmacotherapy, 2017, vol. 18, No. 8, p. 809-817.

Ferini-Strambi, et al., "Effects of reboxetine on sleep and nocturnal cardiac autonomic activity in patients with dysthymia", Journal of Psychopharmacology, 18(3) (2004), p. 417-422, British Association for Phychopharmacology, Sage Publications Ltd., London, UK.

Dauvilliers, et al., "Cataplexy—clinical aspects, pathophysiology and management strategy", Nature Reviews Neurology, 2014; 10 (7): 386 pp. 1-10; 2014.

International Search Report and Written Opinion, PCT/US2019/056134, mailed Jan. 30, 2020.

International Search Report and Written Opinion, PCT/US2025/012527, mailed Feb. 27, 2025.

Melloni, et al., "Potential Antidepressant Agents. a-Aryloxy-Benzyl Derivatives of Ethanolamine and Morpholine", Chem Inform 15 (1984): n. pag.), 1984.

Khan et al., "Calcium Phosphate in Pharmaceutical Product Development", In: Amjad, Z. (eds) Calcium Phosphates in Biological and Industrial Systems, Springer, Boston, MA, https://doi.org/10.1007/978-1-4615-5517-9_ 13, 1998.

Larrosa, O. et al., Stimulant and Anticataplectic Effects of Reboxetine in Patients with Narcolepsy: A Pilot Study, Sleep, 24(3), 282-285, May 2001.

Summary of Product Characteristics, Edronax (reboxetine), last updated on UK electronic Medicines Compendium (eMC), Oct. 23, 2015.

Hajos, M. et al., The Selective Norepinephrine Reuptake Inhibitor Antidepressant Reboxetine: Pharmacological and Clinical Profile, CNS Drug Reviews, 10(1), 23-44, Mar. 2004.

Schmidt, C. et al., The norepinephrine reuptake inhibitor reboxetine is more potent in treating murine narcoleptic episodes than the serotonin reuptake inhibitor escitalopram, Behavioural Brain Research, 308, 205-210, Jul. 2016.

Sepede, G. et al., Reboxetine in clinical practice: a review, Clin Ter., 163(4), e255-e262, Jul. 2012.

U.S. National Library of Medicine, ClinicalTrials.gov Identifier NCT03881852, Clinical Outcomes in Narcolepsy and Cataplexy: An Evaluation of Reboxetine Treatment (CONCERT), 2019; downloaded from: https://clinicaltrials.gov/ct2/show/NCT03881852 on Jul. 17, 2019.

Aloe, F. et al., Brazilian guidelines for the treatment of narcolepsy, Brazilian Journal of Psychiatry, 32(3), 305-314, Sep. 2010.

Doksat et al., A Case of Profound Weight Loss Secondary to use of Reboxetine, J Child Adolesc Behav 2014, 2:3, 2014.

Shands, Drugs & Therapy Bulletin, vol. 21, No. 10, 2007.

Preetha et al., Biphasic Drug Delivery in Controlled Release Formulations—A Review. IJ PT, 6(4), 3046-3060, Apr. 2015.

Edronax, Package Leaflet: Information for the User, 2020.

Sankar et al., What is a missed dose? Implications for construct validity and patient adherence, AIDS Care, 19(6), 775-780, Jul. 2007.

Tabuteau, International Search Report and Written Opinion, PCT/US 2019/056134, mailed Jan. 30, 2020.

Daniels et al., Health-related quality of life in narcolepsy, J. Sleep Res., 10(1), 75-81, Mar. 2001.

International Search Report and Written Opinion, PCT/US2019/037500, mailed Oct. 31, 2019.

International Preliminary Report on Patentability, PCT/US2019/037500, mailed Dec. 30, 2020.

Sateia et al., International Classification of Sleep Disorders, Chest, 146(5), 1387-1394, Nov. 2014.

Kallweit et al., Patient-Reported Measures of Narcolepsy: The Need for Better Assessment, Journal of Clinical Sleep Medicine, 13(5), 737-744, 2017.

International Search Report and Written Opinion, PCT/US2020/062560, mailed Feb. 18, 2021.

(56) References Cited

OTHER PUBLICATIONS

International Preliminary Report on Patentability, PCT/US2019/056134, mailed Apr. 29, 2021.
Thorpy, Recently Approved and Upcoming Treatments for Narcolepsy, CNS Drugs, 34: 9-27, 2020.
Szabo et al., Neurobiological and Immunogenetic Aspects of Narcolepsy: Implications for Pharmacotherapy, Sleep Med Rev. 43: 23-36, Feb. 2019.
Hublin et al., The Ullanlinna Narcolepsy Scale: validation of a measure of symptoms in the narcoleptic syndrome, Journal of Sleep Research, 3(1), 52-59, Mar. 1994.
Ullanlinna Narcolepsy Scale; the printable version accessed online at: healthysleep.med.harvard.edu/narcolepsy/diagnosing-narcolepsy/narcolepsy-self-evaluation, content updated Feb. 2018.
European Extended Search Report and Written Opinion for related application 19874099.5, dated Dec. 7, 2021.
Garcia-Borreguero, D. et al., Effects of Reboxetine in Narcolepsy-Cataplexy: Preliminary findings on 14 patients, Sleep, vol. 24, No. Abstract Supplement, pp. A323-A324, Jun. 2001.
O'Gorman, C. et al., Scientific Rational and Clinical Development of AXS-12 for Narcolepsy, Sleep, vol. 42, No. Abstract Supplement, p. A24, Jan. 2019.
Szakacs, Z. et al., Safety and efficacy of pitolisant on cataplexy in patients with narcolepsy: a randomised, double-blind, placebo-controlled trial, The Lancet Neurology, 16(3), 200-207, Mar. 2017.
Berro, L.F. et al., A journey through narcolepsy diagnosis: From ICSD 1 to ICSD 3, Sleep Science, 7(1), Mar. 2014.
International Preliminary Report on Patentability, PCT/US2020/062560, mailed Jun. 16, 2022.
Lehert, P. et al., Comparing symptom measurement tools in pediatric narcolepsy, Sleep Epidemiology, 2:100032, Dec. 2022.
Arnold et al. Safety and efficacy of esreboxetine in patients with fibromyalgia: an 8-week, multicenter, randomized, double-blind, placebo-controlled study. Clinical therapeutics. Aug. 1, 2010;32(9):1618-32.
Weaver et al. Relationship between Hours of CPAP Use and Achieving Normal Levals of Sleepiness and Daily functioning, Sleep, vol. 30, No. 6, 2007.
Lal et al., Excessive Daytime Sleepiness in Obstructive Sleep Apnea, Mechanisms and clinical Management, Focused Reviews, AnnalsATS vol. 18, No. 5, May 2021.
Bartlett et al. Exploiting chemical Diversity for Drug discovery, RSC Biomolecular / Sciences, The Royal Society of Chemistry 2006, ISBN-10: 0-85404-842-1.
Home, Thesis Resources, Find ETDS, Networked Digital Library of Theses and Dissertations 2023.
Irwin et al. Zinc—A Free Database of Commercially Available Compounds for Virtual Screening, J. Chem. Inf. Model. 2005, 45. 177-182.
Kim et al. PubChem in 2021: new data content and improved web interfaces, Nucleic Acids Research, 2021, vol. 49, D1388-D1395.
STN Registry/Zregistry (CAS Registrysm) Sep. 2016, 2 pages.
Ghimire et al., "In-vitro and In-vivo Erosion Profiles of Hydroxypropylmentylcellulose (HPMC) Matrix Tablets" Journal of Controlled Release, vol. 147 (2010) p. 70-75, Mar. 29, 2010.
Feldman, "Understanding 'Evergreening': Making Minor Modifications of Existing Medications to Extend Protections", Health Affairs, Jun. 2022, 41:6, pp. 801-804.
Dwivedi et al., "Evergreening: A deceptive device in patent rights", Technology in Society 32 (2010), p. 324-330, Department of Biotechnology, Indian Institute of Technology, Guwahati, India.
"Hydroxypropyl Methylcellulose—Processing", NOSB TAP Review Compiled by OMRI, Aug. 26, 2002.
Nokhodchi et al., "The Role of Oral Controlled Release Matrix Tablets in Drug Delivery Systems", Bioimpacts, 2012, 2(4), pp. 175-187, United Kingdom.
Jaspers et al., "Process intensification of pharmaceutical powder blending at commercial throughputs by utilizing semi-continuous mini-blending", International Journal of Pharceutics: X; vol. 8, SP 100264, SN 2590-1567, Elsevier B. V. Jun. 21, 2024.

(S)-2-((S)-(2-ETHOXYPHENOXY)(PHENYL) METHYL)-4-NITROSOMORPHOLINE

CROSS-REFERENCE TO RELATED APPLICATIONS

This application claims the benefit of U.S. Provisional Patent Application No. 63/747,812, filed Jan. 21, 2025; this priority application is incorporated by reference herein in its entirety.

BACKGROUND

Fibromyalgia is a serious and debilitating chronic condition that causes widespread musculoskeletal pain accompanied by fatigue, sleep, memory and mood issues. Fibromyalgia is estimated to afflict an estimated 4 million individuals in the U.S. Fibromyalgia can cause pain, fatigue, muscle pain or tenderness, face and jaw pain, headaches and migraines, digestive problems, including diarrhea and constipation, bladder control issues, memory problems, anxiety, depression, insomnia and other sleep disorders. Unfortunately, currently approved treatments are few for this under-understood condition and are limited by variability in efficacy from patient to patient, tolerability issues, and the need for Drug Enforcement Administration (DEA) scheduling.

SUMMARY

This disclosure relates generally to the treatment of fibromyalgia. For example, a pharmaceutical composition for fibromyalgia, for example, by reducing pain caused by fibromyalgia, may comprise a therapeutically effective amount of esreboxetine free base, or a pharmaceutically acceptable salt thereof, such as esreboxetine succinate, and a pharmaceutically acceptable carrier is disclosed.

One aspect of the present disclosure relates to esreboxetine, such as esreboxetine composition, for example, an esreboxetine composition that is in a tablet dosage form.

Some embodiments include a pharmaceutical composition comprising a uniform blend of esreboxetine and a pharmaceutically acceptable excipient.

Some embodiments comprise a compound represented by a formula:

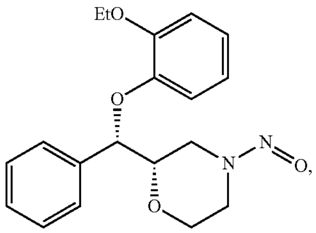 [SMILES: CCOc1ccccc1O[C@@H](c1ccccc1)[C@@H]1CN(N=O)CCO1]

having a name (S)-2-((S)-(2-ethoxyphenoxy)(phenyl) methyl)-4-nitrosomorpholine.

DETAILED DESCRIPTION

The compositions or dosage forms described herein may be useful for treating a nervous system disorder, such as fibromyalgia, and for other purposes.

Detailed descriptions of one or more embodiments are provided herein. It is to be understood, however, that the present disclosure is embodied in various forms. Therefore, specific details disclosed herein are not to be interpreted as limiting, but rather as a basis for the claims and as a representative basis for teaching one skilled in the art to employ the present disclosure in any appropriate manner.

Esreboxetine Tablet Dosage Forms

The dosage form, such as a tablet, may contain esreboxetine free base, such as about 3-5 mg, about 3.5-4.5 mg, or about 4 mg of esreboxetine free base, or a molar equivalent amount of a salt form of esreboxetine, such as about 4-6 mg, about 4-5 mg, or about 5.5 mg of esreboxetine succinate. 5.510 mg of esreboxetine succinate is equivalent to 4 mg of esreboxetine free base.

The dosage form, such as a tablet, may contain hydroxypropyl methylcellulose (HPMC), also referred to as Hypromellose, such as about 30-50%, about 35-45%, or about 40% hydroxypropyl methylcellulose by weight. In some embodiments, the hydroxypropyl methylcellulose is Hypromellose 2208 (Methocel K4M), USP.

The dosage form, such as a tablet, may contain a diluent, such as directly compressible starch. Directly compressible starch contains a blend of about 0.5-2% silicon dioxide and about 98-99.5% starch, such as pregelatinized starch. In some embodiments, the tablet contains about 30-40%, about 30-35%, about 33-34%, or about 33.6% directly compressible starch by weight. For example, StarTab® is a directly compressible starch containing 99% pregelatinized starch and 1% colloidal silicon dioxide. In some embodiments, the directly compressible starch is StarTab® Directly Compressible Starch 4001. In some embodiments, a directly compressible starch, such as StarTab® directly compressible starch (e.g., StarTab® Directly Compressible Starch 4001) may help to improve tablet hardness.

The dosage form, such as a tablet, may contain microcrystalline cellulose, as a binder and/or diluent, such as about 10-30%, about 15-25%, or about 20% microcrystalline cellulose by weight. In some embodiments, the microcrystalline cellulose is Microcrystalline Cellulose (Avicel® PH-102), USP-NF.

The dosage form, such as a tablet, may contain about 0.05-2%, about 0.1-0.2%, or about 0.16% silicon dioxide by weight. In some embodiments, the silicon dioxide is Silicon Dioxide (Syloid® 244FP), USP-NF The dosage form, such as a tablet, may contain magnesium stearate such as about 0.1-5%, about 0.5-1%, or about 0.75% magnesium stearate by weight. In some embodiments, the magnesium stearate is Magnesium Stearate (Hy-Qual®), USP-NF The dosage form, such as a tablet, may be coated, e.g., with a film coating. For example, a film coating may comprise a polymer, a plasticizer, and/or a pigment. The film coating may be, e.g., about 1-10%, about 4-6%, or about 5% of the weight of the dosage form or tablet. In some embodiments, the film coating may be Opadry II 85F520247, Yellow In some embodiments, the dosage form contains esreboxetine free base, such as about 3-5 mg, about 3.5-4.5 mg, or about 4 mg of esreboxetine free base, or a molar equivalent amount of a salt form of esreboxetine, such as about 4-6 mg, about 4-5 mg, or about 5.5 mg of esreboxetine succinate; about 30-50%, about 35-45%, or about 40% hydroxypropyl methylcellulose by weight; about 30-40%, about 30-35%, about 33-34%, or about 33.6% directly compressible starch by weight; about 10-30%, about 15-25%, or about 20% microcrystalline cellulose by weight; about 0.05-2%, about 0.1-0.2%, or about 0.16% silicon dioxide by weight; and about 0.1-5%, about 0.5-1%, or about 0.75% magnesium stearate by weight.

In some embodiments, the dosage form contains esreboxetine free base, such as about 3-5 mg, about 3.5-4.5 mg, or about 4 mg of esreboxetine free base, or a molar equivalent amount of a salt form of esreboxetine, such as about 4-6 mg, about 4-5 mg, or about 5.5 mg of esreboxetine succinate; about 30-50%, about 35-45%, or about 40% hydroxypropyl methylcellulose by weight; about 30-40%, about 30-35%, about 33-34%, or about 33.6% directly compressible starch by weight; about 10-30%, about 15-25%, or about 20% microcrystalline cellulose by weight; about 0.05-2%, about 0.1-0.2%, or about 0.16% silicon dioxide by weight; and the film coating is about 1-10%, about 4-6%, or about 5% of the weight of the dosage form or tablet.

In some embodiments, the dosage form contains esreboxetine free base, such as about 3-5 mg, about 3.5-4.5 mg, or about 4 mg of esreboxetine free base, or a molar equivalent amount of a salt form of esreboxetine, such as about 4-6 mg, about 4-5 mg, or about 5.5 mg of esreboxetine succinate; about 30-50%, about 35-45%, or about 40% hydroxypropyl methylcellulose by weight; about 30-40%, about 30-35%, about 33-34%, or about 33.6% directly compressible starch by weight; about 0.05-2%, about 0.1-0.2%, or about 0.16% silicon dioxide by weight; about 0.1-5%, about 0.5-1%, or about 0.75% magnesium stearate by weight; and the film coating is about 1-10%, about 4-6%, or about 5% of the weight of the dosage form or tablet.

In some embodiments, the dosage form contains esreboxetine free base, such as about 3-5 mg, about 3.5-4.5 mg, or about 4 mg of esreboxetine free base, or a molar equivalent amount of a salt form of esreboxetine, such as about 4-6 mg, about 4-5 mg, or about 5.5 mg of esreboxetine succinate; about 30-50%, about 35-45%, or about 40% hydroxypropyl methylcellulose by weight; about 10-30%, about 15-25%, or about 20% microcrystalline cellulose by weight; about 0.05-2%, about 0.1-0.2%, or about 0.16% silicon dioxide by weight; about 0.1-5%, about 0.5-1%, or about 0.75% magnesium stearate by weight; and the film coating is about 1-10%, about 4-6%, or about 5% of the weight of the dosage form or tablet.

In some embodiments, the dosage form contains esreboxetine free base, such as about 3-5 mg, about 3.5-4.5 mg, or about 4 mg of esreboxetine free base, or a molar equivalent amount of a salt form of esreboxetine, such as about 4-6 mg, about 4-5 mg, or about 5.5 mg of esreboxetine succinate; about 30-40%, about 30-35%, about 33-34%, or about 33.6% directly compressible starch by weight; about 10-30%, about 15-25%, or about 20% microcrystalline cellulose by weight; about 0.05-2%, about 0.1-0.2%, or about 0.16% silicon dioxide by weight; about 0.1-5%, about 0.5-1%, or about 0.75% magnesium stearate by weight; and the film coating is about 1-10%, about 4-6%, or about 5% of the weight of the dosage form or tablet.

In some embodiments, the dosage form contains esreboxetine free base, such as about 3-5 mg, about 3.5-4.5 mg, or about 4 mg of esreboxetine free base, or a molar equivalent amount of a salt form of esreboxetine, such as about 4-6 mg, about 4-5 mg, or about 5.5 mg of esreboxetine succinate; about 30-50%, about 35-45%, or about 40% hydroxypropyl methylcellulose by weight; about 30-40%, about 30-35%, about 33-34%, or about 33.6% directly compressible starch by weight; about 10-30%, about 15-25%, or about 20% microcrystalline cellulose by weight; and about 0.1-5%, about 0.5-1%, or about 0.75% magnesium stearate by weight.

In some embodiments, the dosage form contains esreboxetine free base, such as about 3-5 mg, about 3.5-4.5 mg, or about 4 mg of esreboxetine free base, or a molar equivalent amount of a salt form of esreboxetine, such as about 4-6 mg, about 4-5 mg, or about 5.5 mg of esreboxetine succinate; about 30-50%, about 35-45%, or about 40% hydroxypropyl methylcellulose by weight; about 30-40%, about 30-35%, about 33-34%, or about 33.6% directly compressible starch by weight; about 0.05-2%, about 0.1-0.2%, or about 0.16% silicon dioxide by weight; and about 0.1-5%, about 0.5-1%, or about 0.75% magnesium stearate by weight.

In some embodiments, the dosage form contains esreboxetine free base, such as about 3-5 mg, about 3.5-4.5 mg, or about 4 mg of esreboxetine free base, or a molar equivalent amount of a salt form of esreboxetine, such as about 4-6 mg, about 4-5 mg, or about 5.5 mg of esreboxetine succinate; about 30-50%, about 35-45%, or about 40% hydroxypropyl methylcellulose by weight; about 10-30%, about 15-25%, or about 20% microcrystalline cellulose by weight; about 0.05-2%, about 0.1-0.2%, or about 0.16% silicon dioxide by weight; and about 0.1-5%, about 0.5-1%, or about 0.75% magnesium stearate by weight.

In some embodiments, the dosage form contains esreboxetine free base, such as about 3-5 mg, about 3.5-4.5 mg, or about 4 mg of esreboxetine free base, or a molar equivalent amount of a salt form of esreboxetine, such as about 4-6 mg, about 4-5 mg, or about 5.5 mg of esreboxetine succinate; about 30-40%, about 30-35%, about 33-34%, or about 33.6% directly compressible starch by weight; about 10-30%, about 15-25%, or about 20% microcrystalline cellulose by weight; about 0.05-2%, about 0.1-0.2%, or about 0.16% silicon dioxide by weight; and about 0.1-5%, about 0.5-1%, or about 0.75% magnesium stearate by weight.

In some embodiments, the dosage form contains esreboxetine free base, such as about 3-5 mg, about 3.5-4.5 mg, or about 4 mg of esreboxetine free base, or a molar equivalent amount of a salt form of esreboxetine, such as about 4-6 mg, about 4-5 mg, or about 5.5 mg of esreboxetine succinate; about 30-50%, about 35-45%, or about 40% hydroxypropyl methylcellulose by weight; about 30-40%, about 30-35%, about 33-34%, or about 33.6% directly compressible starch by weight; about 10-30%, about 15-25%, or about 20% microcrystalline cellulose by weight; and the film coating is about 1-10%, about 4-6%, or about 5% of the weight of the dosage form or tablet.

In some embodiments, the dosage form contains esreboxetine free base, such as about 3-5 mg, about 3.5-4.5 mg, or about 4 mg of esreboxetine free base, or a molar equivalent amount of a salt form of esreboxetine, such as about 4-6 mg, about 4-5 mg, or about 5.5 mg of esreboxetine succinate; about 30-50%, about 35-45%, or about 40% hydroxypropyl methylcellulose by weight; about 30-40%, about 30-35%, about 33-34%, or about 33.6% directly compressible starch by weight; about 0.05-2%, about 0.1-0.2%, or about 0.16% silicon dioxide by weight; and the film coating is about 1-10%, about 4-6%, or about 5% of the weight of the dosage form or tablet.

In some embodiments, the dosage form contains esreboxetine free base, such as about 3-5 mg, about 3.5-4.5 mg, or about 4 mg of esreboxetine free base, or a molar equivalent amount of a salt form of esreboxetine, such as about 4-6 mg, about 4-5 mg, or about 5.5 mg of esreboxetine succinate; about 30-50%, about 35-45%, or about 40% hydroxypropyl methylcellulose by weight; about 10-30%, about 15-25%, or about 20% microcrystalline cellulose by weight; about 0.05-2%, about 0.1-0.2%, or about 0.16% silicon dioxide by weight; and the film coating is about 1-10%, about 4-6%, or about 5% of the weight of the dosage form or tablet.

In some embodiments, the dosage form contains esreboxetine free base, such as about 3-5 mg, about 3.5-4.5 mg, or about 4 mg of esreboxetine free base, or a molar equivalent amount of a salt form of esreboxetine, such as about 4-6 mg, about 4-5 mg, or about 5.5 mg of esreboxetine succinate; about 30-40%, about 30-35%, about 33-34%, or about 33.6% directly compressible starch by weight; about 10-30%, about 15-25%, or about 20% microcrystalline cellulose by weight; about 0.05-2%, about 0.1-0.2%, or about 0.16% silicon dioxide by weight; and the film coating is about 1-10%, about 4-6%, or about 5% of the weight of the dosage form or tablet.

In some embodiments, the dosage form contains esreboxetine free base, such as about 3-5 mg, about 3.5-4.5 mg, or about 4 mg of esreboxetine free base, or a molar equivalent amount of a salt form of esreboxetine, such as about 4-6 mg, about 4-5 mg, or about 5.5 mg of esreboxetine succinate; about 30-50%, about 35-45%, or about 40% hydroxypropyl methylcellulose by weight; about 30-40%, about 30-35%, about 33-34%, or about 33.6% directly compressible starch by weight; about 0.1-5%, about 0.5-1%, or about 0.75% magnesium stearate by weight; and the film coating is about 1-10%, about 4-6%, or about 5% of the weight of the dosage form or tablet.

In some embodiments, the dosage form contains esreboxetine free base, such as about 3-5 mg, about 3.5-4.5 mg, or about 4 mg of esreboxetine free base, or a molar equivalent amount of a salt form of esreboxetine, such as about 4-6 mg, about 4-5 mg, or about 5.5 mg of esreboxetine succinate; about 30-50%, about 35-45%, or about 40% hydroxypropyl methylcellulose by weight; about 0.05-2%, about 0.1-0.2%, or about 0.16% silicon dioxide by weight; about 0.1-5%, about 0.5-1%, or about 0.75% magnesium stearate by weight; and the film coating is about 1-10%, about 4-6%, or about 5% of the weight of the dosage form or tablet.

In some embodiments, the dosage form contains esreboxetine free base, such as about 3-5 mg, about 3.5-4.5 mg, or about 4 mg of esreboxetine free base, or a molar equivalent amount of a salt form of esreboxetine, such as about 4-6 mg, about 4-5 mg, or about 5.5 mg of esreboxetine succinate; about 30-40%, about 30-35%, about 33-34%, or about 33.6% directly compressible starch by weight; about 0.05-2%, about 0.1-0.2%, or about 0.16% silicon dioxide by weight; about 0.1-5%, about 0.5-1%, or about 0.75% magnesium stearate by weight; and the film coating is about 1-10%, about 4-6%, or about 5% of the weight of the dosage form or tablet.

In some embodiments, the dosage form contains esreboxetine free base, such as about 3-5 mg, about 3.5-4.5 mg, or about 4 mg of esreboxetine free base, or a molar equivalent amount of a salt form of esreboxetine, such as about 4-6 mg, about 4-5 mg, or about 5.5 mg of esreboxetine succinate; about 30-40%, about 30-35%, about 33-34%, or about 33.6% directly compressible starch by weight; about 10-30%, about 15-25%, or about 20% microcrystalline cellulose by weight; about 0.1-5%, about 0.5-1%, or about 0.75% magnesium stearate by weight; and the film coating is about 1-10%, about 4-6%, or about 5% of the weight of the dosage form or tablet.

In some embodiments, the dosage form contains esreboxetine free base, such as about 3-5 mg, about 3.5-4.5 mg, or about 4 mg of esreboxetine free base, or a molar equivalent amount of a salt form of esreboxetine, such as about 4-6 mg, about 4-5 mg, or about 5.5 mg of esreboxetine succinate; about 30-50%, about 35-45%, or about 40% hydroxypropyl methylcellulose by weight; about 10-30%, about 15-25%, or about 20% microcrystalline cellulose by weight; about 0.1-5%, about 0.5-1%, or about 0.75% magnesium stearate by weight; and the film coating is about 1-10%, about 4-6%, or about 5% of the weight of the dosage form or tablet.

In some embodiments, the dosage form contains esreboxetine free base, such as about 3-5 mg, about 3.5-4.5 mg, or about 4 mg of reboxetine free base, or a molar equivalent amount of a salt form of reboxetine, such as about 4-6 mg, about 4-5 mg, or about 5.5 mg of esreboxetine succinate; about 10-30%, about 15-25%, or about 20% microcrystalline cellulose by weight; about 0.05-2%, about 0.1-0.2%, or about 0.16% silicon dioxide by weight; about 0.1-5%, about 0.5-1%, or about 0.75% magnesium stearate by weight; and the film coating is about 1-10%, about 4-6%, or about 5% of the weight of the dosage form or tablet.

In some embodiments, the composition comprises about 3% to about 6% esreboxetine by weight, or about 3-6%, about 3-3.5%, about 3.5-4%, about 4-4.5%, about 4.5-5%, about 5-5.5%, about 5.5-6%, about 3-4%, about 4-5%, about 5-6% esreboxetine free base by weight, or a molar equivalent amount of a salt form of esreboxetine.

Additional examples of suitable dosage form compositions are listed in Tables 1 and 2 below.

TABLE 1

| Ingredient | % w/w |
|---|---|
| BLEND | |
| Active | 5-6 |
| Release controlling polymer | 35-45 |
| Diluent | 45-60 |
| Glidant | 0.1-0.2 |
| Lubricant | 0.7-0.8 |
| FILM COAT | |
| Film coating | 5 |

TABLE 2

| Ingredient | Function | % w/w |
|---|---|---|
| BLEND | | |
| Esreboxetine Succinate | Active | 5-6 |
| Hydroxypropyl methylcellulose | Release controlling polymer | 35-45 |
| Directly Compressible Starch (1% SiO2, 99% pregelatinized starch) | Diluent | 30-35 |
| Microcrystalline Cellulose | Diluent | 15-25 |
| Silicon Dioxide | Glidant | 0.1-0.2 |
| Magnesium Stearate | Lubricant | 0.7-0.8 |
| FILM COAT | | |
| Blend of polymer, plasticizer, and pigment | Film coating | 5 |

Some dosage forms may comprise a uniform blend of esreboxetine and a pharmaceutically acceptable excipient. In some embodiments, a pharmaceutical composition comprises a uniform blend of esreboxetine and a pharmaceutically acceptable excipient. The excipient may be, for example, a diluent, a binder, a disintegrant, a glidant, a lubricant, or a combination thereof. In some embodiments, a pharmaceutical composition or dosage form may comprise a uniform blend of esreboxetine, a diluent, a binder, and a disintegrant.

A uniform blend includes a blend where samples taken from the powder blender have substantially the same amount of reboxetine. In some embodiments:

when 1 sample is tested from each of 10 locations, such as 10 random locations, in the powder blender where blending occurs, the relative standard deviation (relative standard deviation=[(standard deviation)/(mean)]×100%) of the content of reboxetine for the 10 samples, is 5% or less, 4% or less, or 3% or less; or a) when 3 samples are tested from each of 10 locations, such as 10 random locations, in the powder blender where blending occurs, the relative standard deviation (relative standard deviation=[(standard deviation)/(mean)]×100%) of the content of reboxetine for the 10 samples, is 7% or less, 6% or less, or 5% or less;

In some embodiments, when 10 units of a dosage form, such as 10 tablets, are tested, such as randomly tested, from a single batch, the relative standard deviation (relative standard deviation=[(standard deviation)/(mean)]×100%) of the content of reboxetine for the 10 samples, is 5% or less, 4% or less, or 3% or less.

A composition described herein may be sterilized.

Unless otherwise indicated, any reference to a compound herein, such as reboxetine, by structure, name, or any other means, includes pharmaceutically acceptable salts; alternate solid forms, such as polymorphs, solvates, hydrates, etc.; tautomers; or any other chemical species that may rapidly convert to a compound described herein under conditions in which the compounds are used as described herein.

Some dosage forms containing esreboxetine may contain unacceptable levels of nitroso impurities. (S)-2-((S)-(2-ethoxyphenoxy)(phenyl)methyl)-4-nitrosomorpholine below may be used to determine the quality of a pharmaceutical composition comprising esreboxetine. For example, a sample of a dosage form may be analyzed using a chromatographic method, such as high-performance liquid chromatography (HPLC) or gas chromatography (GC). A sample of (S)-2-((S)-(2-ethoxyphenoxy)(phenyl)methyl)-4-nitrosomorpholine may also be analyzed using a chromatographic method, such as HPLC or GC. This may be useful, for example, for determining the retention time of nitroso impurities, and for determining the sensitivity of the detector or a chromatographic instrument to a nitroso compound. Thus, one method may comprise comparing a chromatographic result obtained from the pharmaceutical composition to a chromatographic result obtained from (S)-2-((S)-(2-ethoxyphenoxy)(phenyl)methyl)-4-nitrosomorpholine.

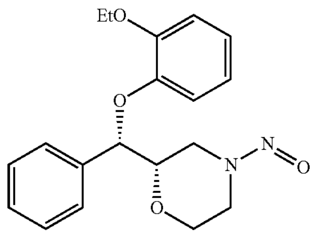 [SMILES: CCOc1ccccc1O[C@@H](c1ccccc1)[C@@H]1CN(N=O)CCO1]

(S)-2-((S)-(2-ethoxyphenoxy)(phenyl)methyl)-4-nitrosomorpholine

In some embodiments, a pharmaceutical composition or dosage form may contain less than 15 ppm of (S)-2-((S)-(2-ethoxyphenoxy)(phenyl)methyl)-4-nitrosomorpholine, such as less than 13 ppm, about 0.5-13 ppm, about 2-5 ppm, about 0.5-2 ppm, about 2-3 ppm, about 3-4 ppm, about 4-5 ppm, about 5-6 ppm, about 6-8 ppm, about 8-10 ppm, or about 10-13 ppm, of (S)-2-((S)-(2-ethoxyphenoxy)(phenyl)methyl)-4-nitrosomorpholine.

The terms "treating" or "treatment" broadly includes any kind of treatment activity, including the diagnosis, cure, mitigation, or prevention of disease in man or other animals, or any activity that otherwise affects the structure or any function of the body of man or other animals. In some embodiments, the mammal being treated is a human being. In some embodiments, the mammal being treated is a non-human mammal, such as a dog, a cat, a mouse, a rat, a rabbit, a monkey, a horse, a pig, etc.

Some embodiments include a method of treating fibromyalgia, comprising administering a dosage form or pharmaceutical composition described herein to a human being having fibromyalgia with a visual analog pain scale score of at least about 40 nm on a 100 nm scale.

Some embodiments include a method of treating fibromyalgia, comprising administering a dosage form or pharmaceutical composition described herein to a human being in need thereof, wherein a daily dose of about 2 mg to about 6 mg of esreboxetine is administered for at least one week, at least two weeks, at least three weeks, at least four weeks, at least 5 weeks, or at least 6 weeks, wherein the human being experiences a reduction in fibromyalgia pain during the course of the treatment, as measured by a visual analog scale (VAS) score, that is greater than the reduction in pain that the human being would have experienced by administering a placebo.

Some embodiments include a method of treating fibromyalgia, comprising administering a dosage form or pharmaceutical composition described herein to a human being in need thereof, wherein a daily dose of about 2 mg to about 6 mg of esreboxetine is administered for at least one week, at least two weeks, at least three weeks, at least four weeks, at least 5 weeks, or at least 6 weeks, wherein the human being experiences a reduction in pain during the course of the treatment, as measured by a visual analog scale (VAS) score, that is greater than the reduction in pain that the human being would have experienced by administering a placebo.

Some embodiments include a method of treating fibromyalgia, comprising administering a dosage form or pharmaceutical composition described herein to a human being in need thereof, wherein a daily dose of about 2 mg to about 6 mg of esreboxetine is administered for at least one week, at least two weeks, at least three weeks, at least four weeks, at least 5 weeks, or at least 6 weeks, wherein the human being experiences a reduction in pain during the course of the treatment, as measured by a visual analog scale (VAS) score, that is greater than the reduction in pain that the human being would have experienced by administering a placebo.

A composition described herein may be used to treat a condition such as an arthritic disorder, including a pain disorder, nervous system disorder, including an addictive disorder (including those due to alcohol, nicotine, and other psychoactive substances), a withdrawal syndrome, an adjustment disorder (including depressed mood, anxiety, mixed anxiety and depressed mood, disturbance of conduct, and mixed disturbance of conduct and mood), depression (including major depressive disorder, alone or in combination with other antidepressants), an age-associated learning or mental disorder (including Alzheimer's disease), anorexia nervosa apathy, an attention-deficit (or another cognitive) disorder due to general medical conditions, attention-deficit hyperactivity disorder (ADHD), bipolar disorder, bulimia nervosa, chronic fatigue syndrome, chronic or acute stress, chronic pain, conduct disorder, cyclothymic disorder, depression (including adolescent depression and minor depression), dysthymic disorder, fibromyalgia and other somatoform disorders (including somatization disorder, conversion disorder, pain disorder, hypochondriaism, body dysmorphic disorder, undifferentiated somatoform disorder, and somatoform NOS), generalized anxiety disorder (GAD), incontinence (i.e., stress incontinence, genuine stress incontinence, and mixed incontinence), stress urinary incontinence, an inhalation disorder, an intoxication disorders (alcohol addiction), mania, migraine headaches, obesity (e.g., reducing the weight of obese or overweight patients), an obsessive compulsive disorder or a related spectrum disorder, oppositional defiant disorder, panic disorder, peripheral neuropathy, post-traumatic stress disorder, premenstrual dysphoric disorder (i.e., premenstrual syndrome and late luteal phase dysphoric disorder), a psychotic disorder (including schizophrenia, negative symptoms of schizophrenia, schizoaffective or schizophreniform disorder, either alone or as an adjuvant therapy), seasonal affective disorder, a sleep disorder (such as narcolepsy, including narcolepsy with cataplexy, or enuresis), social phobia (including social anxiety disorder), a specific developmental disorder, selective serotonin reuptake inhibition (SSRI) "poop out" syndrome (i.e., wherein a patient who fails to maintain a satisfactory response to SSRI therapy after an initial period of satisfactory response), TIC disorders (e.g., Tourette's Disease), post-shingles pain, painful diabetic peripheral neuropathy, postherpetic neuralgia, syncope, and/or vasovagal syncope, etc.

Specific dosages maybe adjusted depending on conditions of disease, the age, body weight, general health conditions, sex, and diet of the subject, dose intervals, administration routes, excretion rate, and combinations of drugs.

In some embodiments, a human patient is treated with a dosage form or composition described herein, such as a dosage form of Table 1 or 2, e.g., containing about 3-5 or about 3.5 mg to about 4.5 mg of esreboxetine succinate, or a molar equivalent of another salt form, or a molar equivalent amount of the free base form (e.g., 4 mg of esreboxetine free base), e.g., once daily, to treat fibromyalgia.

NON-LIMITING EXAMPLES

Specifically Contemplated Embodiments

The following are examples of embodiments that are specifically contemplated by the inventor:

Embodiment 1. A compound represented by a formula:

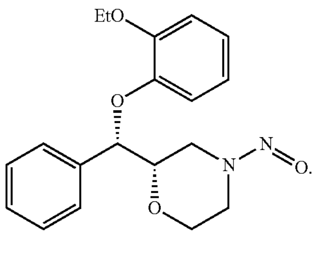 [SMILES: CCOc1ccccc1O[C@@H](c1ccccc1)[C@@H]1CN(N=O)CCO1]

Embodiment 2. A method of determining the quality of a pharmaceutical composition comprising esreboxetine, comprising comparing a chromatographic result obtained from the pharmaceutical composition to a chromatographic result obtained from the compound of clause 1.

Embodiment 3. A dosage form comprising esreboxetine and less than 13 ppm of a compound represented by a formula:

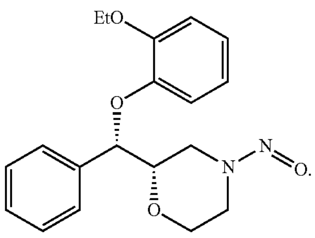 [SMILES: CCOc1ccccc1O[C@@H](c1ccccc1)[C@@H]1CN(N=O)CCO1]

Embodiment 4. The dosage form of embodiment 3, further comprising hydroxypropyl methylcellulose.

Embodiment 5. The dosage form of any preceding embodiment, further comprising directly compressible starch.

Embodiment 6. The dosage form of any preceding embodiment, further comprising microcrystalline cellulose.

Embodiment 7. The dosage form of any preceding embodiment, further comprising silicon dioxide.

Embodiment 8. The dosage form of any preceding embodiment, further comprising magnesium stearate.

Embodiment 9. The dosage form of any preceding embodiment, further comprising a film coating.

Embodiment 10. The dosage form of any preceding embodiment, further comprising hydroxypropyl methylcellulose, and directly compressible starch.

Embodiment 11. The dosage form of any preceding embodiment, further comprising hydroxypropyl methylcellulose and microcrystalline cellulose.

Embodiment 12. The dosage form of any preceding embodiment, further comprising directly compressible starch and microcrystalline cellulose.

Embodiment 13. The dosage form of any preceding embodiment, further comprising hydroxypropyl methylcellulose, directly compressible starch and microcrystalline cellulose.

Embodiment 14. The dosage form of any preceding embodiment, comprising about 3% to about 6% esreboxetine by weight.

Embodiment 15. The dosage form of any preceding embodiment, further comprising about 35% to about 45% hydroxypropyl methylcellulose by weight.

Embodiment 16. The dosage form of any preceding embodiment, further comprising about 30% to about 35% directly compressible starch by weight.

Embodiment 17. The dosage form of any preceding embodiment, further comprising about 15% to about 25% microcrystalline cellulose by weight.

Embodiment 18. The dosage form of any preceding embodiment, further comprising about 0.1% to about 0.2% silicon dioxide by weight.

Embodiment 19. The dosage form of any preceding embodiment, further comprising about 0.7% to about 0.8% magnesium stearate by weight.

Embodiment 20. The dosage form of any preceding embodiment, further comprising about 5% of the film coating by weight.

As used herein in the specification and in the claims, the articles "a" and "an" are used to refer to one or to more than one (i.e., to at least one) of the grammatical object of the article unless the context clearly indicates otherwise. By way of example, "an element" means one element or more than one element.

As used herein in the specification and in the claims, the phrase "and/or," should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of," or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

Wherever the phrase "for example," "such as," "including," and the like are used herein, the phrase "and without limitation" is understood to follow unless explicitly stated otherwise. Similarly, "an example," "exemplary," and the like are understood to be non-limiting.

The invention claimed is:

1. A dosage form comprising esreboxetine, or a pharmaceutically acceptable salt thereof, and less than 13 ppm of a compound represented by a formula.

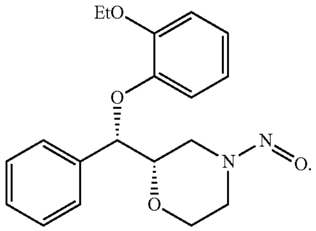 [SMILES: CCOc1ccccc1O[C@@H](c1ccccc1)[C@@H]1CN(N=O)CCO1]

2. The dosage form of claim 1, further comprising hydroxypropyl methylcellulose.

3. The dosage form of claim 1, further comprising directly compressible starch.

4. The dosage form of claim 1, further comprising microcrystalline cellulose.

5. The dosage form of claim 1, further comprising silicon dioxide.

6. The dosage form of claim 1, further comprising magnesium stearate.

7. The dosage form of claim 1, further comprising a film coating.

8. The dosage form of claim 1, further comprising hydroxypropyl methylcellulose and directly compressible starch.

9. The dosage form of claim 1, further comprising hydroxypropyl methylcellulose and microcrystalline cellulose.

10. The dosage form of claim 1, further comprising directly compressible starch and microcrystalline cellulose.

11. The dosage form of claim 1, further comprising hydroxypropyl methylcellulose, directly compressible starch and microcrystalline cellulose.

12. The dosage form of claim 1, comprising about 3% to about 6% esreboxetine, or a pharmaceutically acceptable salt thereof, by weight.

13. The dosage form of claim 1, further comprising about 35% to about 45% hydroxypropyl methylcellulose by weight.

14. The dosage form of claim 1, further comprising about 30% to about 35% directly compressible starch by weight.

15. The dosage form of claim 1, further comprising about 15% to about 25% microcrystalline cellulose by weight.

16. The dosage form of claim 1, further comprising about 0.1% to about 0.2% silicon dioxide by weight.

17. The dosage form of claim 1, further comprising about 0.7% to about 0.8% magnesium stearate by weight.

18. The dosage form of claim 1, further comprising about 5% of the film coating by weight.

19. A dosage form comprising esreboxetine succinate and less than 13 ppm of a compound represented by a formula:

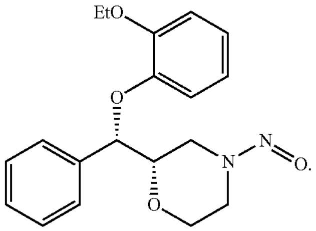 [SMILES: CCOc1ccccc1O[C@@H](c1ccccc1)[C@@H]1CN(N=O)CCO1]

20. The dosage form of claim 19, further comprising starch.

21. The dosage form of claim 19, further comprising silicon dioxide.

22. The dosage form of claim 19, further comprising magnesium stearate.

* * * * *